United States Patent [19]
van de Winkel

[11] Patent Number: 6,111,166
[45] Date of Patent: Aug. 29, 2000

[54] TRANSGENIC MICE EXPRESSING HUMAN FCα AND β RECEPTORS

[75] Inventor: J. G. J. van de Winkel, Odijk, Netherlands

[73] Assignee: Medarex, Incorporated, Annandale, N.J.

[21] Appl. No.: 08/884,541

[22] Filed: Jun. 27, 1997

Related U.S. Application Data

[63] Continuation-in-part of application No. 08/309,322, Sep. 19, 1994, abandoned.

[51] Int. Cl.$^7$ .............................. A61K 67/02; C12Q 1/68; C12N 15/85

[52] U.S. Cl. ................................... 800/18; 800/9; 800/13; 800/24; 435/6; 435/69.6; 435/320.1; 435/355; 435/455; 435/375

[58] Field of Search .............................. 800/8, 9, 18, 21, 800/3, 24, 25, 13; 435/320.1, 6, 69.6, 361, 375, 455; 536/23.1

[56] References Cited

U.S. PATENT DOCUMENTS

| | | | |
|---|---|---|---|
| 4,954,617 | 9/1990 | Fanger et al. | 530/384 |
| 5,610,057 | 3/1997 | Shen et al. | 435/334 |
| 5,635,600 | 6/1997 | Fanger et al. | 530/387.3 |

FOREIGN PATENT DOCUMENTS

| | | |
|---|---|---|
| 0 255 249 | 2/1988 | European Pat. Off. . |
| WO 91/00360 | 1/1991 | WIPO . |
| WO 91/05805 | 5/1991 | WIPO . |
| WO 92/05793 | 4/1992 | WIPO . |
| WO 94/10332 | 5/1994 | WIPO . |
| WO 95/15376 | 6/1995 | WIPO . |
| WO 95/24220 | 9/1995 | WIPO . |
| WO 95/28959 | 11/1995 | WIPO . |
| WO 96/40789 | 12/1996 | WIPO . |

OTHER PUBLICATIONS van de Winkel. Journal of Biological Chemistry. 266 (20): 13449–13455, 1991.
de Wit. Journal of Immunology. 155: 1203–1209, 1995.
Heijnen et al. Journal of Clinical Investigation. 97(2): 331–338, Jan. 1996.
Greenspan et al. Journal of Immunology. 150(8–2):66A, 1993.
Ravetch et al. Annual Review of Immunology. 9: 457–92, 1991.
Fung–Leung et al. Journal of Experimental Medicine. 183: 49–56, Jan. 1996.
Kinet et al. Proceedings of the National Academy of Sciences. 85: 6453–6487, 1988.
Shimizu et al. Proceedings of the National Academy of Sciences. 85: 1907–1911, 1988.
Mullins et al. Journal of Clinical Investigation. 98(11): S37–40, 1996.
Strojek et al. Genetic Engineering: Principles and Methods. Plenum Press. 10: 221–246, 1988.

Ashworth, L. et al.,"An Integrated Metric Physical Map of Human Chromosome 19", *Nature Genetics*, vol. 11, pp. 422–427 (1995).

Anderson, C. et al.,"Stimulation of Superoxide Production by a Monoclonal Antibody (mab) Against the High Affinity IgG Fc Receptor (FcRI) of U937 Cells", *Fed. Proc.*, vol. 45, Abstract #3247, pp. 714 (1986).

Ball, E. et al.,"Initial Trail of Bispecific Antibody–Mediated Immunotherapy of CD15 Bearing Tumors: Cytotoxicity of Human Tumor Cells Using a Bispecific Antibody Comprised of Anti–CD15 (MoAb PM81) and Anti–CD64/FcγRI (MoAb 32)", *J. of Hematotherapy*, vol. 1, pp. 85–94 (1992).

Chen, J. et al., "An Immunoconjugate of Lys3–Bombesin and Monoclonal Antibody 22 Can Specifically Induce FcgammaRI (CD64)–Dependent Monocyte– and Neutrophil–Mediated Lysis of Small Cell Carcinoma of the Lung Cells" *Clinical Cancer Research*, vol. 1 (4), pp. 425–434 (1995).

Clark, M. et al., "Use of Bispecific Monoclonal Antibodies to Treat Hematological Malignancies: A Model System Using CD3 Transgenic Mice", *Bispecific Antibodies and Targeted Cellular Cytotoxicity*, Edited by Romet–Lemonne et al., Fondation Nationale de Transfustion Sanguine, Les Ulis, France, pp. 243–247 (1990).

Deo, Y. et al., "Clinical Significance of IgG Fc Receptors and Fcγ–directed Immunotherapies", *Immunology Today*, vol. 18 (3), pp. 127–135 (1997).

de Palazzo, I. et al.,"Potentiation of Tumor Lysis by a Bispecific Antibody that Binds to CA19–9 Antigen and the Fcγ Receptor Expressed by Human Large Granular Lymphocytes", *Cancer Research*, vol. 50, pp. 7123–7128 (1990).

de Wit, T. et al.,"Structure of the Gene for the Human Myeloid IgA Fc Receptor (CD89)", *Journal of Immunology*, vol. 155, pp. 1203–1209 (1995).

Ericson, S. et al., "The Effect of Recombinant Human Interleukin–3 and Recombinant Human Granulocyte–macro–Phage Colony–Stimulating Factor on Fcγ Receptor Expression and Antibody–Dependent Cellular Cytotoxicity of Hematopoietic Progenitor Cells During in Vitro Myeloid Maturation", *Experimental Hematology*, vol. 22, pp. 283–289 (1994).

Fanger, M. et al., "Production and Use Of Anti–FcR Bispecific Antibodies" *Immunomethods* vol. 4 (1), pp. 72–81 (1994).

Fanger, M. et al., "Fcγ Receptors in Cancer and Infectious Disease", *Immunol. Res.*, vol. 11, pp. 203–216 (1992).

Fanger, M. et al., "Bispecific Antibodies" *Critical Reviews in Immunology*, vol. 12 (3,4), pp. 101–124 (1992).

(List continued on next page.)

Primary Examiner—John L. LeGuyader
Assistant Examiner—Carrie Stroup
Attorney, Agent, or Firm—Lahive & Cockfield, LLP; Jane E. Remillard, Esq.; Giulio A. DeConti, Jr., Esq.

[57] ABSTRACT

Transgenic animals expressing Fc receptors and uses for the animals in testing the efficacy of human antibodies and in generating novel antibodies are described.

2 Claims, No Drawings

OTHER PUBLICATIONS

Graziano, R. et al., "Construction and Characterization of a Humanized Anti–Gamma–Ig Receptor Type I (Fcgamma RI) Monoclonal Antibody" *The Journal of Immunology*, vol. 155 (10): 4996–5002 (1995).

Guyre, P. et al., "Monoclonal Antibodies that Bind to Distinct Epitopes on FcγRI are able to Trigger Receptor Function", *The Journal of Immunology*, vol. 143 (5), pp. 1650–1655 (1989).

Guyre, P. et al., "Recombinant Immune Interferon Increases Immunoglobulin G Fc Receptors on Cultured Human Mononuclear Phagocytes", *Journal of Clinical Investigation*, vol. 72, pp. 393–397 (1983).

Isturiz, M. et al., "Two Different Fcγ Receptor–Dependent Cytotoxic Mechanisms Triggered by Monoclonal Immunoglobulins", *Immunology Letters*, vol. 29, pp. 271–276 (1991).

Jung, Gundram, et al., "Target Cell–Induced T cell Activation with Bi– and Trispecific Antibody Fragments", *Eur. J. Immunol.*, vol. 21, pp. 2431–2435 (1991).

Keler, T. et al., "Bispecific Antibody (MDX–210) Targeting of Tumor Cells to Monocytes Via the Fc Receptor Type I (FcγRI) Promotes Antibody Dependent Cellular Cytotoxicity (ADCC) and Induction of Specific Cytokines," *Proceedings of the American Association for Cancer Research*, vol. 36, 485 (1995).

Keler, T. et al., "Bispecific Antibody–dependent Cellular Cytotoxicity of HER2/neu–overexpressing Tumor Cells by Fcγ Receptor Type I–expressing Effector Cells", *Cancer Research*, vol. 57, pp. 4008–4014 (1997).

Kubagawa, H. et al., "Cloning of Genes Encoding Possible Murine Fcα Receptors (FcαR)," *FASEB J.*, vol. 8, No. 4–5, A749 (1994).

Looney, R. et al., "Human Monocytes and U937 Cells Bear Two Distinct Fc Receptors for IgG", *The Journal of Immunology*, vol. 136 (5), pp. 1641–1647 (1986).

Lubeck, M. et al., "The Interaction of Murine IgG Subclass Proteins with Human Monocyte Fc Receptors", *The Journal of Immunology*, vol. 135 (2), pp. 1299–1304 (1985).

Mabondzo, A. et al., "Antibody–dependent Cellular Cytotoxicity and Neutralization of Human Immunodeficiency Virus Type 1 by High Affinity Corss–Linking of gp41 to Human Macrophage Fc IgG Receptor Using Bispecific Antibody", *Journal of Virology*, vol. 75, pp. 1451–1456 (1994).

Monteiro, R. et al., "Definition of Immunoglobulin A Receptors on Eosinophils and their Enhanced Expression in Allergic Individuals," *J. Clin Invest.*, vol. 92, 1681–1685 (1993).

Monteiro, R. et al., "Molecular Heterogeneity of Fcα Receptors Detected by Receptor–Specific Monoclonal Antibodies," *The Journal of Immunology*, vol. 148, No. 6, 1764–1770 (1992).

Morton, C. et al.,"Structure and Function of Human IgA Fc Receptors (FcαR)", *Critical Reviews in Immunology*, vol. 16, pp. 423–440 (1996).

Patry, C. et al., "Fcα Receptors Mediate Release of Tumour Necrosis Factor–α and Interleukin–6 by Human Monocytes Following Receptor Aggregation," *Immunology*, vol. 86, 1–5 (1995).

Patry, C. et al.,"Identification of Fcα Receptor (CD89) Isoforms Generated by Alternative Splicing that are Differentially Expressed Between Blood Monocytes and Alveolar Macrophages", *Journal of Immunology*, vol. 156, pp. 4442–4448 (1996).

Pfefferkorn, L. and Yeaman, G., "Association of IgA–Fc Receptors (FcαR) with FcεRIγ2 Subunits in U937 Cells," *The Journal of immunology*, vol. 153, 3228–3236 (1994).

Repp, R. et al., "G–CSF Stimulated Neutrophils As Effector Cells In Immunotherapy With A Bispecific Antibody to FcgammaRI and To HER–2/neu (MDX210): Preclinical Studies", *Immunobiology*, vol. 191 (2–3): 250–251 (1994).

Sarmay, G. et al., "Mapping and Comparison of the Interaction Sites on the Fc region of IgG Responsible for Triggering Antibody Dependent Cellular Cytotoxicity (ADCC) Through Different Types of Human Fcγ Receptor", *Molecular Immunology*, vol. 29 (5), pp. 633–639 (1992).

Shen, L. et al., "Direct Stimulation of ADCC by cloned Gamma Interferon is not Ablated by Glucocorticoids: Studies Using a Human Monocyte–like Cell Line (U–937)", *Molecular Immunology*, vol. 21 (2), pp. 167–173 (1984).

Shen, L. et al., "Heteroantibody–Mediated Cytotoxicity: Antibody to the High Affinity Fc Receptor for IgG Mediates Cytotoxicity by Human Monocytes that is Enhanced by Interferon–γ and is not Blocked by Human IgG", *The Journal of Immunology*, vol. 137 (11), pp. 3378–3382 (1986).

Shen, L., "Receptors for IgA on Phagocytic Cells," *Immunol. Res.*, vol. 11, 273–282 (1992).

Shen, L. et al., "My 43, A Monoclonal Antibody That Reacts with Human Myeloid Cells Inhibits Monocyte IgA Binding and Triggers Function," *Journal of Immunology*, vol. 143, No. 12, 4117–4122 (1989).

Shimada, T. et al., "Comparative Analysis of FcαR on Neutrophils and Monocytes," *FASEB J.*, vol. 9, No. 4, A804 (1995).

Shimo, K. et al., "Ligand–Binding Properties of Recombinant Soluble Fcα Receptor," *FASEB J.*, vol. 9, No. 4, A774 (1995).

Stockmeyer, B. et al.,"Preclinical Studies with FcγR Bispecific Antibodies and Granulocyte Colony–stimulating Factor–primed Neutrophils as Effector Cells Against HER–2/neu Overexpressing Breast Cancer", *Cancer Research*, vol. 57, pp. 696–701 (1997).

Threlkeld, S.C. et al., "Differential Down–Modulation of IgA Fc Receptors (FcαR) on Neutrophils and Monocytes in HIV–Infected and Normal Individuals," *FASEB J.*, vol. 8, No. 4–5, A492 (1994).

Valerius, T. et al., "Involvement of the High–Affinity Receptor for IgG (FcγRI; CD64) in Enhanced Tumor Cell Cytotoxicity of Neutrophils During Granulocyte Colony–Stimulating Factor Therapy", *Blood*, vol. 82 (3), pp. 931–939 (1993).

Valone, F. et al., "Phase Ia/Ib Trial of Bispecific Antibody MDX–210 in Patients with Advanced Breast or Ovarian Cancer that Overexpresses the Proto–Oncogene HER–2/neu," *J Clin Oncol*, vol. 13, No. 9, 2281–2292 (1995).

Valone, F.H. et al., "Schedule Dependent Immunological Stimulation by Bispecific Antibody (BsAb) MDX–210 (anti–FcγRI x anti–HER–2/neu) in Patients with Breast or Ovarian Cancers that Over Express HER–2/neu," *Proceedings of the American Association for Cancer Research*, vol. 36, 500 (1995).

van de Winkel, et al.,"Gene Organization of the Human High Affinity Receptor for IgG, FcγRI (CD64)", *The Journal of Biological Chemistry*, vol. 266 (20), pp. 13449–13455 (1991).

van de Winkel, J. et al., "Human IgG Fc Receptor Heterogeneity: Molecular Aspects and Clinical Implications", *Immunology Today*, vol. 14 (5), pp. 215–221 (1993).

Weisbart, R.H. et al., "GM–CSF Induces Human Neutrophil IgA–Mediated Phagocytosis by an IgA Fc Receptor Activation Mechanism," *Nature*, vol. 332, 647–648 (1988).

Yeaman, G. and Pfefferkorn, L.C., "IgA–Fc Receptors (FcαR) on U937 Cells Associate with FcεRI Gamma Subunits," *FASEB J.*, vol. 8, No. 4–5, A981 (1994).

Ingmar, A.F.M. et al, "Antigen Targeting to Myeloid–specific Human FcγRI/CD64 Triggers Enhanced Antibody Responses in Transgenic Mice," *J. Clin. Invest.*, vol. 97, No. 2, 331–338 (1996).

Flamand, V. et al, "Delayed maturation of cd4–cd8–Fc–gamma–RII–III+T and natural killer cell precursors in Fc–ε–RI–γ transgenic mice," *J. Exp. Med.*, 184:1725–1735, (1996).

Guyre, P. M. et al, "Increased potency Fc–receptor–targeted antigens," *Cancer Immunology Immunotherapy*, 45:146–148, (1997).

Heijnen, I.A.F.M. et al., "Antigen targeting to myeloid–specific human Fc–gamma–RI–CD64 triggers enhanced antibody responses in transgenic mice cd," *J. Clin. Invest.*, 97:331–338, (1996).

Scharenberg, A. M. et al., "The FcRβ subunit functions as an amplifier of FcRγ mediated cell activation signal," *J. Allergy and Clin. Immun.*, 99:s406, (1997).

TRANSGENIC MICE EXPRESSING HUMAN FCα AND β RECEPTORS

RELATED APPLICATIONS

This application is a continuation-in-part of U.S. Ser. No. 08/309,322, filed Sep. 19, 1994, now abandonded, the contents of which is incorporated by reference.

BACKGROUND OF THE INVENTION

Several types of effector cells, such as monocytes, neutrophils, and natural killer (NK) cells, have cell surface receptors that bind the Fc portion of immunoglobulins (Igs). When such cells encounter target cells that have been opsonized with immunoglobulin antibodies, they form conjugates, and either lyse or phagocytose the target cells, depending upon the effector cell type, the target cell type and the specific Fc receptor type (FcR) involved.

It has been demonstrated that target cell conjugation with an effector cell and lysis can also be induced by a covalently cross-linked bispecific heteroantibody made up of both anti-Fc receptor antibody and antibody directed against a target cell epitope. When effector cells bind such heteroaggregates to their Fc receptor, they can specifically bind and lyse target cells which have not been opsonized, but which express the appropriate target antigen (See e.g. U.S. patent application Ser. No: 972,871; Karpovsky et al. (1984) *J Exp. Med.* 160:1686–1701). Segal et al. have reported cytolysis of tumor cells by mouse monocytes with an attached heteroantibody which joins the Fc receptor of the monocyte on one end with tumor cell epitopes on the other end (See U.S. Pat. No. 4,676,980). Recently, a variety of bispecific monoclonal antibodies and immunotoxins have been shown to confer antitumor effects in vitro as well in vivo (See e.g., World Patent No: 9208892; Pan et al (1990) *J Immunol.*, 145:267–275; Trail et al. (1993) Science (Washington, D.C.), 261:212–215; Weiner et al. (1993) *J Immunol.*, 151:2877–2886; Link et al. (1993) *Blood*, 81:3343–3349; and Vallera, D. A. (1994) *Blood*, 83:309–317).

The binding of a heteroantibody to FcR is mediated by the Fc region of the antibody. This binding is ordinarily susceptible to inhibition by physiological concentrations of immunoglobulin. However, monoclonal antibodies, which bind to a site on the Fc receptor distinct from the binding site for endogenous immunoglobulin, have been produced (see, for example, Anderson et al., *J Biol. Chem.* 261:12856 (1986); and Shen et al., *J Immunol.* 137:3378–3382 (1986)). These antibodies are useful as the effector-specific moiety of heteroantibodies, because serum immunoglobulin does not interfere with targeted effector cell killing.

Methods for making novel antibodies to the Fc receptor or in vivo methods for testing the efficacy of an antibody for administration in humans would be useful.

SUMMARY OF THE INVENTION

The present invention provides transgenic non-human animals expressing human Fc receptors (FcR), and methods for making and using the transgenic animals (e.g., to test anti-human FcR binding, generate high affinity antibodies etc.).

Accordingly, in one aspect, the invention features a non-human transgenic animal which expresses a human Fc receptor (FcR). The Fc receptor type can be human Fcγ (e.g., FcγRI, FcγRII or FcγRIII), Fcα (e.g., FcαRI), or Fcε (e.g., FcεRI or FcεRII). In one embodiment, expression of the human FcR is controlled by endogenous human regulatory sequences which naturally flank the FcR gene in humans, and which control expression patterns and levels of FcR.

Transgenic non-human animals (e.g., mammals) of the invention can be of a variety of species including murine (rodents (e.g., mice, rats), avian (chicken, turkey, fowl), bovine (beef, cow, cattle), ovine (lamb, sheep, goats), porcine (pig, swine), and piscine (fish). In a preferred embodiment, the transgenic animal is a rodent, such as a mouse or a rat.

In another aspect, the invention features methods for using non-human transgenic animals which express human Fc receptors. For example, the animals can be used as accurate animal models for studying human FcR function, such as anti-human FcR binding and FcR-mediated immune functions. Alternatively, the animals can be used to generate antibodies, such as anti-human FcR antibodies or antibodies specific for a particular antigen, or other immune reactions.

Accordingly, in one embodiment, the transgenic animals of the invention are used to test antibodies for binding to human FcR by administering the antibody to the transgenic non-human animal and then detecting (e.g., in vitro in a blood sample taken from the animal) antibody binding to FcR on FcR expressing cells. This method can be used, for example, to test the safety of an antibody (e.g., a humanized antibody) for in vivo clinical use.

In another embodiment, the transgenic animals are used to test the ability of anti-human FcR antibodies (e.g., monospecific, bispecific, tri-specific, multi-specific) to target molecules (e.g., antigens or cells) to Fc receptor expressing cells for e.g., killing or phagocytosis of the target molecule by the FcR expressing cell. For example, the animals can be used to test the ability of an anti-human Fc antibody, linked to or specific for an antigen, to target the antigen to an Fc receptor-bearing immune cell.

In yet another embodiment, the transgenic animals of the invention are used to detect the ability of an anti-human FcR antibody (e.g., mono-, bi-, tri- or multispecific) to generate an immune response as indicated by, for example, by an increase in the level of a cytokine or an antibody.

In still another embodiment, the transgenic animals are used to generate high affinity human antibodies specific for a particular antigen by coupling the antigen to an anti-human Fc receptor antibody to obtain a antibody antigen conjugate, immunizing the transgenic animal with the conjugate, and then selecting (e.g., isolating) an antibody specific to the antigen from e.g., a body sample taken from the animal. In one embodiment, the antigen is poorly immunogenic.

In yet another embodiment, the transgenic animals are used to generate high affinity human antibodies specific for a particular antigen (e.g., a poorly immunogenic antigen) by crossing the transgenic animal with a compatible non-human transgenic animal capable of making human antibodies to generate a founder and administering an antigen to the founder to generate antibodies specific for the antigen.

Other features and advantages of the instant invention will become more apparent from the following detailed description and claims.

DETAILED DESCRIPTION OF THE INVENTION

The present invention is based, in part, on the finding that microinjection of a nucleic acid encoding a human Fc receptor, e.g., FcγRIa (CD64) or FcαRI (CD89), under control of endogenous (e.g., human) regulatory sequences, into the pronucleus of fertilized mouse eggs produced founder mice expressing functional human Fc receptors on macrophages, monocytes and neutrophils, but not on other blood cells (e.g. lymphocytes). This expression pattern is similar to that found in humans. Moreover, it was found that the regulation of human FcR expression in transgenic mice was also similar to that in humans, and that the expressed human FcR was functionally competent (e.g., interacted with mouse signaling molecules). These results demonstrated the generation of non-human transgenic animals which were highly accurate models of human FcR receptor systems.

Definitions

As used herein, the following terms and phrases shall have the meanings set forth below:

"Transgenic animal" is intended to include any non-human animal in which one or more of the cells of the animal contain heterologous nucleic acid encoding a human Fc receptor, that has been introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

The term "non-human animals" is intended to include any vertebrate such as mammals; birds; reptiles; and amphibians. Suitable mammals include: rodent, non-human primates, sheep, dogs and cows. Suitable birds include chickens, geese, and turkeys. Preferred non-human animals are selected from the rodent family including rat and mouse, most preferably mouse.

As used herein, the term "transgenic cell" refers to a cell containing a transgene.

As used herein, the term "transgene" means a nucleic acid sequence (encoding, e.g., a human Fc receptor), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The term "transgenic gene construct" comprises a nucleic acid molecule, e.g., a vector, containing the subject gene, e.g., the FcR gene, operably linked in a manner capable of replicating and expressing the gene in a host cell. The FcR gene construct can be introduced into a non-human animal cell by nucleic acid-mediated gene transfer.As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant FcR gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of a naturally-occurring form of FcR.

A "substantially pure" nucleic acid is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by polymerase chain reaction (PCR) or restriction endonuclease treatment) independent of other DNA sequences. Substantially pure DNA also includes a recombinant DNA which is part of a hybrid gene encoding additional Fc receptor sequences.

"Homology," or "sequence identity," as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or have sequence identity at that position. The percent of homology or sequence identity between two sequences is a function of the number of matching or homologous positions shared by the two sequences divided by the number of positions compared x 100. For example, if 6 of 10, of the positions in two sequences are matched or homologous then the two sequences are 60% homologous or have 60% sequence identity. By way of example, the DNA sequences ATTGCC and TATGGC share 50% homology or sequence identity. Generally, a comparison is made when two sequences are aligned to give maximum homology or sequence identity.

The terms "peptides," "proteins," and "polypeptides" are used interchangeably herein.

A transgene of the present invention causes cells of a non-human animal transformed with the transgene to express a recombinant form of an Fc receptor, e.g., a human Fc receptor (such as FcRI, FcRII or FcRIII) recognizing any antibody isotype (e.g. α, γ or ε). As used herein, the term "Fc receptor" or "FcR" includes a member of the family of Multi-chain Immune Recognition Receptors (MIRR), consisting of distinct ligand binding α-chains, which non covalently associate with shared signaling components. The signaling molecules include FcR γ-, β- or ζ- chains.

In preferred embodiments, the Fc receptor is a human FcγR (e.g., FcγRI, FcγRII or FcγRIII), FcαRI, or FcεR (e.g., FcεRI or FcεRII).

In other preferred embodiments, the transgene expresses a human IgG receptor, e.g., an Fc-gamma receptor (FcγR). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the transgene expresses a human high affinity FcγRI. The human FcγRI is a 72 kDa molecule, which shows high affinity for monomeric IgG ($10^8$–$10^9 M^{-1}$).

In still other preferred embodiments, the trangene expresses a human IgA receptor, e.g., an Fc-alpha receptor (FcαR (CD89)). The term "IgA receptor" is intended to include the gene product of one α-gene (FcαRI) located on chromosome 19. This gene is known to encode several alternatively spliced transmembrane isoforms of 55 to 110 kDa. Fc αRI (CD89) is constitutively expressed on monocytes/macrophages, eosinophilic and neutrophilic granulocytes, but not on non-effector cell populations. FcαRI has medium affinity ($\approx 5 \times 10^7 M^{-1}$) for both IgA1 and IgA2, which is increased upon exposure to cytokines such as G-CSF or GM-CSF (Morton, H. C. et al. (1996) *Critical Reviews in Immunology* 16:423–440).

In still other preferred embodiments, the transgene expresses a human IgE receptor, e.g., FcεRI or FcεRII (Ravetech, J. V. and J. P. Kinet (1991) *Annu. Rev. Immunol.* 9: 457). The nucleotide sequence of the α- chain of FcεR are disclosed, e.g. in Shimizu, A. et al., (1988) *Proc. Natl. Acad. Sci. USA* 85:1907–1911; Kinet, J.-P. et al., (1987) *Biochemistry* 26:4605–4610; International Patent Application WO 89/05352.

In one preferred embodiment of the invention, the distribution of FcR, e.g., human FcR, expressed by the transgenic animal is similar to the distribution of the FcR in human cells. As used herein, the term "distribution" refers to the pattern of cell-type distribution. For example, human FcαRs are known to be present on monocytes, macrophages, neutrophils, and other myeloid cells. FcαRs are also known to be found on metamyelocytes, myelocytes, promyelcytes and some myeloblasts from, e.g., bone marrow. Human FcγRI is expressed in monocytes, macrophages, neutrophils and dendritic cells.

As used herein, the term "regulation" is intended to include any characteristic pattern of FcR gene expression in response to a signal, e.g., up- or downregulation of gene or protein expression on an effector cell by extracellular signals, e.g., humoral factors, e.g., cytokines; chemicals, e.g., vitamins. In preferred embodiments, the regulation of expression of the FcR transgene mirrors the regulation of expression of the endogenous receptor in a cell, e.g., a human cell. For example, expression of FcαRs can be increased by stimulation of myeloid cells. As an illustration, stimulation of U937 cells and PLB985 cells with Phorbol Myristic Acetate (PMA) increases the cell surface level of FcαR several folds (Maliszewski, et al. (1990) *J Exp. Med.* 172:1665). Other agents which can increase the surface level of FcαRs include calcitriol, 1–25 dihydroxyvitamin D3, and tumor necrosis factor-α (TNF-α). In other instances, the expression of FcαR may not change in response to an extracellular signal, e.g., a cytokine, e.g., G-CSF.

In other examples, expression of FcγRI has been found to be up-regulated by interferon gamma (IFN-γ) and G-CSF. This enhanced expression increases the cytotoxic activity of FcγRI cells against targets.

In preferred embodiments, transgenically expressed human FcRs retain similar functional properties as are exhibited in human cells. For example, the transgenic FcR is preferably capable of mediating at least one Fc-receptor mediated effector cell function. The term "Fc-receptor mediated effector cell function" is intended to include any effector function, which is triggered by binding of immunoglobulin, e.g., IgA or IgG, to an Fc receptor on an effector cell. For example, binding of an immunoglobulin, e.g., IgA or IgG, to cells bearing transgenically expressed human FcαRs or FcγRs can induce a variety of effector functions, such as phagocytosis, antibody dependent cellular cytotoxicity (ADCC), antigen presentation, inflammatory mediator release, lysozyme production, and superoxide anion production (Maliszewski, et al. (1990) *J Exp. Med.* 172:1665). In other embodiments, the affinity of the transgenically expressed human FcRs may be modulated, e.g., enhanced or reduced, in response to an extracellular signal, e.g., a cytokine, e.g., G-CSF or GM-CSF, in a similar fashion as an FcR in a human cell.

A "bispecific molecule" or "bispecific antibody" is intended to include a molecule, which minimally comprises a first binding determinant which recognizes an Fc receptor, e.g., an antibody or a fragment thereof that is capable of binding to an Fc receptor (FcR) on a effector cell; and a second binding determinant which recognizes a cell surface molecule on a target cell, e.g., a receptor, a cell surface antigen. Exemplary second binding determinants include an antibody, a fragment thereof, a genetic construct, or a ligand.

As used herein, the term "multispecific molecule" encompasses bispecific molecules, but also includes molecules having more than two binding determinants. For example, a multispecific molecule can include an "anti-enhancement factor (anti-EF) portion". The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target. The "anti-enhancement factor portion" can bind an $F_c$ receptor or a target.

In preferred embodiments, the antibody may be whole, i.e. having heavy and light chains or any fragment thereof, e.g., Fab or (Fab')$_2$ fragment. The antibody further may be a light chain or heavy chain dimer, or any minimal fragment thereof such as a Fv or a single chain construct as described in Ladner et al. U.S. Pat. No. 4,946,778, issued Aug. 7, 1990, the contents of which is expressly incorporated by reference. The term "monoclonal antibody" or "monoclonal antibody composition" as used herein refers to a preparation of antibody molecules of single molecular composition. A monoclonal antibody composition displays a single binding specificity and affinity for a particular epitope.

The term "antibody" as used herein is also intended to include chimeric, human, single chain and humanized antibodies, as well as binding fragments of such antibodies or modified versions of such antibodies. A "chimeric antibody" is intended to include an antibody in which the variable regions are from one species of animal and the constant regions are from another species of animal. For example, a chimeric antibody can be an antibody having variable regions which derive from a mouse monoclonal antibody and constant regions which are human. A "humanized antibody" or fragment includes any human antibody capable of retaining non-human hypervariable regions, also termed, the complementarity-determining regions (CDRs), for example, antibodies in which the CDRs are from one species of animal and the framework regions and constant regions of the antibody are from a different animal species. In a humanized antibody, the CDRs can be from a mouse monoclonal antibody and the other regions of the antibody are human. In preferred embodiments, a human antibody is derived from known proteins NEWM and KOL for heavy chain variable regions (VHs) and REI for Ig kappa chain, variable regions (VKs).

In preferred embodiments, the anti-Fcγ receptor antibody is a human monoclonal antibody, the binding of which is not blocked by human immunoglobulin G (IgG). The production and characterization of these preferred monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. Anti-FcγRI mAb 22, F(ab')$_2$ fragments of mAb 22, and can be obtained from Medarex, Inc. (Annandale, N.J.). In other embodiments, the anti-Fcγ receptor antibody is a humanized form of monoclonal antibody 22. The humanized mab 22 antibody producing cell line was deposited at the American Type Culture Collection on Nov. 4, 1992 under the designation HA022CL1 and has the accession no. CRL 11177.

In other embodiments, the anti-FcR antibody is specific for an FcαR. Exemplary monoclonal antibodies include My 43, A77, A62, A59, and A3 (Monteiro et al. (1992) *J Immunol.* 148:1764; Shen et al. (1989) *J Immunol.* 143: 4117). Preferred anti-FcαR antibody are capable of binding to an FcαR without being inhibited by IgA. The antibody A77 has been produced by immunizing mice with acrylamide gel slices containing FcαcR that was IgA affinity purified from human cell lysates. Monoclonal antibodies were screened according to three characteristics: staining of U937 cells at a higher density after PMA activation, selective reactivity with blood monocytes and granulocytes, and their ability to immunoprecipitate molecules of approximately 55 to 75 kDa from neutrophils and activated U937 cells.

In other embodiments, the ligand can be any ligand that interacts with a molecule. In a preferred embodiment, the ligand binds a protein, e.g., a surface protein on a target cell, such as a cancer cell. Preferred ligands include ligands to receptors, such as growth or differentiation factors. For example, a bispecific or multispecific molecule can comprise an epidermal growth factor, or at least a portion or modified form that is capable of interacting with a receptor, e.g., an epidermal growth factor receptor. In another preferred embodiment of the invention, the ligand is a small peptide, such as bombesin, gastrin-releasing peptide (GRP), litorin, neuromedin B, or neuromedin C. The sequences of the peptides can be found, e.g., in U.S. Pat. No. 5,217,955, the content of which is incorporated herein by reference. The ligand can also be a modified form of any of these peptides. The modification can increase binding to the receptor, decrease binding, or not affect the binding to a receptor. The modification of the ligand can also transform an agonist into an antagonist, such that the ligand inhibit rather than stimulate cell proliferation. The modification of the ligand can be an addition, a deletion, a substitution, or a modification of at least one amino acid.

The bispecific or multispecific molecules can be prepared by conjugating the anti-FcR and anti-target portions using methods known in the art. For example, a variety of coupling or cross-linking agents can be used for covalent conjugation. Examples of cross-linking agents include protein A, carbodiimide, N-succinimidyl-S-acetyl-thioacetate (SATA), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J Exp. Med.* 160:1686; Liu, MA et al. (1985) *Proc. Natl. Acad. Sci.* USA 82:8648). Other methods include those described by Paulus (Behring Ins. Mitt. (1985) No. 78, 118–132); Brennan et al. (*Science* (1985) 229:81–83), and Glennie et al. (*J Immunol.* (1987) 139: 2367–2375). Preferred conjugating agents are SATA and sulfo-SMCC, both available from Pierce Chemical Co. (Rockford, IL).

The bispecific molecule can also be a single chain bispecific molecule, such as a single chain bispecific antibody, a single chain bispecific molecule comprising one single chain antibody and a ligand, or a single chain bispecific molecule comprising two ligands. Multivalent molecules can also be single chain molecules or may comprise at least two single chain molecules. Methods for preparing bi- or multivalent antibodies are for example described in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

An "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. In preferred embodiments, an effector cell is capable of inducing antibody-dependent cellular toxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

"Target cell" shall mean any undesirable cell in a subject (e.g., a human or animal) that can be targeted by a bi- or multispecific molecule. Examples of target cells include a cancer or a tumor cell, an antibody producing lymphocytes for treatment of an autoimmune disease, an IgE producing lymphocyte for treatment of an allergy, or a pathogen infected cell.

Exemplary cancer or tumor cells of the various organ systems include those malignant cells from the lung, breast, ovarian, lymphoid, gastrointestinal, head and neck, pancreas, liver, genito-urinary tract, kidney, colon cancers, rectum, renal-cell carcinoma, bone, blood, lymphatic system, prostate and/or testicular tumors, non-small cell carcinoma of the lung, cancer of the small intestine, central nervous system and cancer of the esophagus. Suitable targets among cancer cell antigens are preferably members of the human EGF-like receptor family, more preferably the cancer cell antigen is an EGF receptor, and most preferably the cancer cell antigen is HER-2/neu, HER-3, HER-4, or a heteromultimeric receptor comprised of at least one HER subunit. Additional preferred cancer cell antigens include carcinoembryonic antigen, gastrin releasing peptide receptor antigen, and TAG 72.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In certain embodiments, the cancer cell is from hematopoietic origin, e.g., arising from myeloid, lymphoid or erythroid lineages, or precursor cells thereof. Exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97). Lymphoid malignancies which may be treated by the subject method include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF) and Hodgkin's disease.

The target can also be a pathogen, e.g., a microorganism, e.g., a virus, bacterium, fungus, protozoa, or a soluble antigen (such as rheumatoid factor or other auto-antibodies).

Additionally, the target portion may comprise or be directed against an antigen. A preferred embodiment contains an antigen that can be used to induce a specific immune response against a chronic infection, against a tumor or cancer cell, or to deplete antigen in the circulation.

Transgenic animals of the present invention are highly accurate models of FcR expression and function in humans. Accordingly, these animals are useful in a number of different ways to study the mechanisms behind human FcR function and related events, and to generate and test products (e.g., antibodies, bispecifics, multispecifics etc.) useful in treating and diagnosing human diseases.

Accordingly, in one embodiment, the transgenic animals of the invention are used to test antibodies and multi- or bispecific molecules (e.g., for human safety and efficacy) for binding to target epitopes, such as a region of a human FcR, an antigen, or both. For example, the initiation of an immune response in the transgenic animal upon administration of such molecules indicates that the molecules will produce the same effect in humans. An immune response in a host can be detected for example by an increased level of a cytokine, production of an antibody or a T cell response. The transgenic animal can be engineered to contain target cells (e.g. tumor, virus) prior to administration of the multi- or bispecific molecule.

To detect antibody binding following administration of an anti-Fc antibody, or anti-Fc bi- or multispecific molecule to a transgenic animal, any suitable assay can be used. For example, a sample of the animals blood can be taken and assayed for the presence of anti-Fc antibody-FcR complexes using screening assays known in the art, such as an enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. Accordingly, in the present invention, these assays are used to detect FcR-antibody complexes formed between immunoglobulins (e.g., IgG, IgA etc.) contained in the animal's blood serum and human FcR contained on the surface of particular cells in the animal.

The FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radio-immunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

To detect an immune response following administration of an anti-Fc antibody, or anti-Fc bi- or multispecific molecule to a transgenic animal, any suitable procedure for measuring a change in the concentration of e.g., a cytokine, antibody or T cell population in the plasma or serum of the animal can be used. For example, a change in a cytokine concentration in vivo can be detected via a variety of immunoassays, such as enzyme immunoassay (EIA) or radioimmunoassay (RIA). Exemplary cytokines that can be assayed include: granulocyte/macrophage colony stimulating factor (GM-CSF), granulocyte colony-stimulating factor (G-CSF), macrophage colony-stimulating factor (M-CSF), interleukins 1–12 (IL-1 to IL-12).

For example, plasma can be obtained form a transgenic animal to which an antibody, bispecific, or multi specific molecule has been administered. The concentration of a cytokine can be measured using an EIA by detecting the interaction of the cytokine with an antibody, which is in turn conjugated to an enzyme. The activity of the enzyme is detected by the reaction with an appropriate substrate, preferably a chromogenic substrate, in such a manner as to produce a chemical moiety which can be detected, for example, by spectrophotometric, fluorimetric or by visual means (Voller, "The Enzyme Linked Immunosorbent Assay (ELISA)", Diagnostic Horizons 2:1–7, 1978, Microbiological Associates Quarterly Publication, Walkersville, MD; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, FL, 1980; Ishikawa, et al., (eds.) Enzyme Immunoassay, Kgaku Shoin, Tokyo, 1981). Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection of a cytokine may also be accomplished using a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

It is also possible to label the anti-cytokine antibody with a fluorescent compound. When the fluorescently labeled antibody is exposed to light of the proper wave length, its presence can then be detected. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

A non-human transgenic animal of the present invention expressing a human Fc receptor can further provide an indication of the safety of a particular humanized antibody for administration to a human. For example, a humanized antibody can be administered to the transgenic animal and the binding of the antibody to the human Fc receptor expressed by the animal can be detected as an indication that the humanized antibody is safe (i.e. will not elicit an immune response) for in vivo human use.

As used herein, the term "administration," is intended to include any route of introducing a composition, e.g., a humanized antibody, into a subject. Examples of routes of administration which can be used include injection (subcutaneous, intravenous, parenterally, intraperitoneally, intrathecal, etc.), oral, inhalation, rectal and transdermal. The pharmaceutical preparations are of course given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the composition can be coated with or disposed in a selected material to protect it from natural conditions which may detrimentally effect its ability to perform its intended function. The composition can be administered alone, or in conjunction with either another agent as described above or with a pharmaceutically acceptable carrier, or both. The compound can be administered prior to the administration of the other agent, simultaneously with the agent, or after the administration of the agent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion. The phrases "systemic administration," "administered systemically", "peripheral administration" and "administered peripherally" as used herein mean the administration of a composition, such that it enters the subject's system and, thus, is subject to metabolism and other like processes, for example, subcutaneous administration.

An antibody, bispecific or multispecific molecule can be administered to a subject (e.g., transgenic animal) in the form of a pharmaceutical composition in conjunction with a pharmaceutically acceptable carrier. As used herein, the phrase "pharmaceutically acceptable carrier" is intended to include substances that can be coadministered with a multispecific molecule and allows the molecule to perform its intended function.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phen asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the multispecific molecule in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

The transgenic animals expressing human Fc receptors as described herein can also be used to generate high affinity human antibodies particularly to poorly immunogenic antigens. For example, an antigen can be coupled to an anti-Fc receptor antibody to obtain a antibody antigen conjugate. A variety of coupling or cross-linking agents can be found above in the description of the preparation of bispecific molecules which can be used for covalent conjugation of an anti-Fc receptor antibody to obtain a antibody antigen conjugate. The conjugate can then be used to immunize a non-human transgenic animal expressing a human Fc receptor. Antibodies specific to the antigen can then be selected using known techniques.

Methods for immunizing a non-human transgenic animal are known in the art. (See, for example, *Antibodies: A Laboratory Manual* ed. by Harlow and Lane (Cold Spring Harbor Press: 1988)). For example, a non-human transgenic animal, such as a trangenic mouse, can be immunized with an immunogenic form of an protein or a peptide, e.g., antibody antigen conjugate. Techniques for conferring immunogenicity on a protein or peptide include conjugation to carriers or other techniques known in the art. An antibody antigen conjugate can be administered in the presence of adjuvant. The progress of immunization can be monitored by detection of antibody titers in plasma or serum. Standard ELISA or other immunoassays can be used with the immunogen as antigen to assess the levels of antibodies.

High affinity human antibodies can alternatively be generated by crossing a non-human transgenic animal expressing a human Fc receptor with a compatible (i.e. an animal of the same species but opposite sex) non-human transgenic animal capable of making human antibodies (e.g. as described in Bruggeman et. al., (1993) *Year Immunol* 7:33–40; Tuaillon et. al., (1993) *PNAS* 90:3720–3724; Bruggeman et. al., (1991) *Eur. J Immunol*. 21:1323–1326 and Wood et. al., WO 91/00906) to generate a founder and administering an antigen to the founder to generate novel antibodies.

In addition, the transgenic animals described herein can be used to assess the role of Fc receptors in mucosal immunity and allergic processes.

Transgenic Animals

Detailed methods for generating non-human transgenic animal are described herein and in the section entitled "Examples" below. Transgenic gene constructs can be introduced into the germ line of an animal to make a transgenic mammal. For example, one or several copies of the construct may be incorporated into the genome of a mammalian embryo by standard transgenic techniques.

Any non-human animal can be used in the methods described herein. Preferred mammals are rodents, e.g., rats or mice.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, the Fc receptor transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

The progeny of the transgenically manipulated embryos can be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of an Fc receptor. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

DNA Constructs

The Fc receptors can be expressed from a construct which includes regulatory sequences specific for the receptor, e.g., an human FcR promoter, e.g., a human FcγR promoter, e.g., a human FcγR promoter, and a nucleic acid encoding the FcR, e.g., human FcγR or human FcαR. Preferably, these regulatory sequences are genomic in origin, and include one or more introns. For example, the transgenic construct can include regulatory regions located in the 5'-flanking regions of a gene encoding FcR, e.g., an FcγR or an FcαR, operably linked to the FcR coding sequences in a manner capable of replicating and expressing the gene in a host cell. If additional flanking sequence are useful in optimizing expression, such sequences can be cloned using the existing sequences as probes. Additional sequences necessary for maximizing processing of the transgene can be derived from either cDNA or genomic sequences.

The gene organization of the human FcRs has been described (Tepler, I. et al. (1989) *J Biol. Chem.* 264: 5912–15; J. van de Winkel et al. (1991), *J Biol. Chem.* 266 (20): 13449–455; de Wit et al. (1995) *J Immunol.* 155: 1204–1209). For example, the gene encoding the prototypic human FcαRI (CD89) consists of five exons and four introns that span approximately 12 kilobase pairs: a leader peptide which is encoded by two exons, the second of which is 36 bp long an specifies the predicted peptidase cleavage site; the third and fourth exons which code for two homologous Ig-like domains; and a final exon which encodes a short extracellular region, a hydrophobic transmembrane region, and a short cytoplasmic tail. The 5'- flanking region for the human FcαRI has also been mapped, as well as the transcription initiation sites (de Wit et al. (1995) *J Immunol.* 155: 1204–1209).

An expression system or construct described herein can also include a 3' untranslated region downstream of the DNA sequence. Such regions can stabilize the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the Fc receptor untranslated region or other 3' untranslated sequences well known in the art. Preferably, the 3' untranslated region is derived from an Fc receptor. The length of the 3' untranslated region is not critical but the stabilizing effect of its poly A transcript appears important in stabilizing the RNA of the expression sequence.

Optionally, the expression system or construct includes a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they appear to be useful in improving the level of expression.

Expression systems can be prepared using methods known in the art. An expression system can be prepared as part of a larger plasmid. Such preparation allows the cloning and selection of the correct constructions in an efficient manner as is known in the art. Expression systems can be located between convenient restriction sites on the plasmid so that they can be easily isolated from the remaining plasmid sequences for incorporation into the desired mammal.

The various methods employed in the preparation of the plasmids and transformation of host organisms are known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLES

Example 1

Generation of Human FcγRI-Transgenic Mice

To generate human FcγRIa transgenic mice, a genetic construct coding for the human FcγRIa (CD64) was microinjected into the pronucleus of fertilized mouse eggs. The construct was was a 13 kB genomic fragment (phage 1) containing endogenous human regulatory sequences, cloned from human leukocyte DNA using the method of Van de Winkel, J.G.J., L. K. Ernst, C. L. Anderson and I. M. Chiu, *J. Biol. Chem.* (1991) 266:13449–13455. The nucleotide sequence of the 5'-flanking region of the construct is provided by Van de Winkel, supra., including the sequences containing the transcription initiation sites responsible for constitutive and inducible transcription of the FcγRIa gene. The 13 kB fragment was cloned into pTZ18 plasmid (Pharmacia), released from the vector by restriction endonuclease digestion, and purified by agarose gel electrophoresis and electroelution.

The gene organization of FcγRIa consits of five introns and six exons and spans 9.4 kb pairs: the leader sequence is encoded by two exons, the second of which is 21 base pairs long and contains the predicted site of the peptidase cleavage; the third, fourth, and fifth exons, each encode homologous Ig-like extracellular domains; the hydrophobic transmembrane region and a highly charged cytoplasmic tail are encoded by a final exon (Van de Winkel, supra).

The final DNA concentration was adjusted to 4 µg/ml. Fertilized mouse eggs were recovered in cumulus from the oviducts of superovulated FVB/N females that had mated with males several hours earlier. The DNA fragments were injected into the most accessible pronucleus of each fertilized egg using the method of Van Lohuizen, M., S. Verbeek, P. Krimpenfort, J. Domen, C. Saris, T. Radaszkiewicz and A. Berns, *Cell* (1989) 56:673–682. After overnight culturing, 2-cell stage embryos were implanted into the oviducts of day 1 pseudopregnant foster animals and carried to term. Several weeks after birth of animals that had developed from microinjected eggs, total genomic DNA was prepared from tail biopsies using the method of Hogan, B.L.M., F. Constantini and E. Lacy, Cold Spring Harbor, New York: Cold Spring Harbor Laboratory (1986).

This DNA was digested with HindII enzyme, separated on agarose gels, blotted and probed with human FcγRI cDNA p135 (Allen, J.M. and B. Seed, *Science* (1989) 243:378–380). Two positive founders were identified, coded 1852 and 1853.

Example 2

Characterization of Human FcγRI-Transgenic Mice

Two independent transgenic lines were generated, and in both lines human FcγRI was highly expressed on peritoneal macrophages, and at lower levels on monocytes. One line (1852) also expressed low levels of human FcγRI on neutrophils, which was not observed in line 1853. All other blood cells (e.g. lymphocytes) were negative for human FcγRI-expression.

Incubation of mouse cells with Interferon-γ or Interleukin-10 showed enhanced expression of human FcγRI on monocytes/macrophages, while Interleukin-4 downregulated regulated human FcγRI-expression. These cytokines showed similar effects on huFcγRI upon injection in vivo. In addition, injection of Granulocyte Colony Stimulating Factor (G-CSF) triggered increased expression of human FcγRI in vivo, but not in vitro.

Overall, these results showed the human FcγRI molecule to be expressed in exactly the same types of cells in both transgenic mice and humans (i.e., similar distribution patterns of FcγRI in transgenic mice and humans). In addition, the regulation of receptor expression in transgenic mice was similar to that in humans. Thus, the correct endogenous human regulatory elements were both present and functional in transgenic mice, making these transgenic models very accurate and valuable indicators of the human system.

In addition, it was shown that human FcγRI expressed in transgenic mice was functionally competent and interacted with mouse signaling molecules (e.g., FcR γ chain). Specifically, the human FcγRI molecule was shown to bind its physiological ligand (i.e., FITC-conjugated human IgG). Functional studies using bispecific antibodies targeting human FcγRI specifically showed human FcγRI to be active in both phagocytosis and antibody dependent cellular cytotoxicity (ADCC) as described below. In particular, a M22× anti-Her-2/neu bispecific antibody was tested for ADCC of Her-2/neu-targeted human SK-BR3 cells. The bispecific antibody M22×anti-Her-2/neu which contains Fab' gamma fragments of anti-FcγRI antibody (monoclonal antibody 22) crosslinked to an Fab fragment of anti-Her-2/neu monoclonal antibody (520C9) was prepared using the method of Glennie, M.J. et al. (1987) *J Immunol.* 139:2367. A bispecific antibody M22×anti-ox red blood cell (RBC) Fab antibody (described in Anderson et al. (1991) *J Exp. Med.*) was additionally tested for ADCC.

Macrophages expressing human FcγRI in transgenic mice showed a decrease in mouse Fcγ receptors (measured by monoclonal antibody 2.4G2) which can be explained by competition for receptor signaling subunits (e.g. FcRγ chain). Injection of human FcγRI transgenic mice with humanized anti-FcγRI antibody (monoclonal 22) triggered a very rapid mouse anti-human antibody response. More importantly, most antibodies were of the IgG (and not the IgM type), which demonstrated that antigen uptake via huFcγRI is highly effective.

In conclusion, the studies described herein demonstrate that transgenic mice expressing human FcγRI are accurate models for studying human FcγRI function in vivo.

Example III

Generation of Human FcαRI-Transgenic Mice

To generate human FcαRI transgenic mice, a genetic construct coding for the human FcαRI (CD89) receptor was microinjected into the pronucleus of fertilized mouse eggs. The genetic construct was a 37 Kb genomic fragment (cosmid clone R31931) cloned from human chromosome 19 as described by Ashworth, L. K., Batzer, M. A. et al., *Natural Genetics* (1995) 11:422–427. The fragment contained endogenous regulatory sequences and was released from the vector by SfiI restriction endonuclease digestion.

The gene encoding human FcαR (CD89) consists of five exons and four introns that span approximately 12 kilobase pairs: a leader peptide which is encoded by two exons, the second of which is 36 bp long an specifies the predicted peptidase cleavage site; the third and fourth exons which code for two homologous Ig-like domains; and a final exon which encodes a short extracellular region, a hydrophobic transmembrane region, and a short cytoplasmic tail. The 5'-flanking region for the human FcαRI have also been mapped, along with the transcription initiation sites (de Wit et al. (1995) *J Immunol.* 155: 1204–1209).

To prepare transgenic mice, a final DNA concentration was adjusted to 4 μg/ml. Fertilized mouse eggs were recovered in cumulus from the oviducts of superovulated FVB/N females that had mated with males several hours earlier. The DNA fragments were injected into the most accessible pronucleus of each fertilized egg using the methods of Van Lohuizen, M., S. Verbeek, P. Krimpenfort, J. Domen, C. Saris, T. Radaszkiewicz and A. Berns, *Cell* (1989) 56:673–682. After overnight culturing, 2-cell stage embryos were implanted into the oviducts of day 1 pseudopregnant foster animals and carried to term. Several weeks after birth of animals that had developed from microinjected eggs, total genomic DNA was prepared from tail biopsies using the methods of Hogan, B.L.M., F. Constantini and E. Lacy, Cold Spring Harbor, New York: Cold Spring Harbor Laboratory (1986).

To identify transgenic mice, genomic DNA was prepared from tail biopsies, digested with EcoRI enzyme, separated on agarose gel, blotted and probed with human FcαRI cDNA as described in Maliszewski, C.R., March, C.J. et al., *J Exp. Med.* (1990) 172:16–65. Three positive founders were obtained, referred to as 2106, 2107 and 2126.

Example IV

Characterization of the Human FcαRI-Transgenic Mice

Two independent transgenic lines were generated using founders 2107 and 2126. Expression of human FcαRI was high on neutrophils, moderate on monocytes and negative on lymphocytes. Thus, the human FcαcRI expression pattern in these transgenic lines was similar to expression of FcαRI on human cells, which show constitutive expression of FcαRI on monocytes, macrophages, eosinophilic and neutrophilic granulocytes (Morton, H.C. (1996) *Critical Reviews in Immunology* 16:423–440). Transgenic line 2126 showed a higher expression of human FcαRI on neutrophils than line 2107. In addition, injection of Granulocyte Colony Stimulating Factor (G-CSF) did not increase expression of human FcαRI in vivo, mirroring the regulation of FcαR in response to G-CSF on human cells.

Overall, these results demonstrate that the regulatory elements of the human FcαRI were both present and functionally active in the transgenic mice, as evidenced by e.g., similarities in the cellular distribution patterns and regulation of human FcαRI between the trangenic mice and humans. Thus, transgenic mice expressing human FcαRI of the present invention provide highly accurate models for human systems.

Example V

Functional Characterization of Human FcαRI-Transgene

Functional studies showed the transgenically expressed human FcαRI to be active in both phagocytosis of yeast (Candida albicans) by neutrophils using the bispecific antibody A77×anti-Candida. The A77 antibody is described in Monteiro et al. (1992) *J. Immunol.* 148:1764. In addition, these studies showed the transgenically expressed human Fc αRI to be active in antibody dependent cellular cytotoxicity (ADCC) using the bispecific antibody A77×anti-Her-2/neu to target human SK-BR3 cells. The protocols describing these functional studies are described below. These results demonstrate that human FcαRI receptors expressed in transgenic mice were functionally competent in mediating, for example, phagocytosis of yeast cells and cytotoxic activity, providing further accuracy as models for studying the mechanism of FcαRI receptors in vivo.

Candida Phagocytosis Assays

Candida albicans (strain ATCC 448585) was cultured overnight at 37° C. in Sabouraud Maltose Broth (Difco, Detroit, MI), harvested by centrifugation, washed trice in PBS, and labeled by incubation with FITC (Sigma, St. Louis, MO) at a concentration of 0.1 mg/mL in 0.1 mol/L $NaH_2PO_4/Na_2HPO_4$ buffer (pH 9.6) for 30 minutes at 4° C. After three washed with PBS, $5 \times 10^5$ yeast particles were incubated for 30 minutes at 37° C. with $2 \times 10^5$ isolated PMN without or with 10 μg/mL [A77×α Candida] bispecific antibody. Candida albicans phagocytosis was quantitated by measuring FITC-fluorescence intensities of cells on a flow cytometer using PE-conjugated CD11b MoAb (Becton Dickinson, San Jose, CA) as a gate marker for PMN. Alternatively, phagocytes was determined in cytospin preparations evaluated by microscopy.

Antibody Dependent Cellular Cytotoxicity Assays

Target cells were labelled with 200 μCi for 2 hours. Whole blood, isolated effector cells (50 μL), sensitizing antibodies 0.4 μg/mL, for bispecific antibody anti-Fcα antibody×anti-Her-2/neu (A77 Fab×520C9 Fab) and RF10+ were added into round-bottom microtiter plates. Assays were started by adding target cell suspensions (50 μL), giving a final volume of 200 μL, and an effector to target cell ratio of 80:1 with isolated cells. After 3 hours at 37° C., assays were stopped by centrifugation, and Cr release from triplicates was measured.

Percentage of cellular cytotoxicity was calculated using the formula:

$$\% \text{ specific lysis} = \frac{\text{experimental cpm} - \text{basal cpm}}{\% \text{ lysis without FcR antibody}} \times 100$$

Negative values determined by this formula are reported as "% stimulation" in the presence of Fc receptor antibody.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A transgenic mouse which expresses the human FcαRI receptor gene operably linked to human regulatory sequences, wherein the mouse is characterized by expression of said receptors on neutrophils and monocytes.

2. A transgenic mouse which expresses the human FcγRI receptor gene operably linked to human regulatory sequences, wherein the mouse is characterized by expression of said receptors on macrophages and monocytes.

* * * * *

UNITED STATES PATENT AND TRADEMARK OFFICE
CERTIFICATE OF CORRECTION

PATENT NO. : 6,111,166
DATED : August 29, 2000
INVENTOR(S) : J.G.J. van de Winkel It is certified that error appears in the above-indentified patent and that said Letters Patent is hereby corrected as shown below:

On the Title Page, Item [54] and Column 1, line 1 should read:

TRANSGENIC MICE EXPRESSINGHUMAN Fcα and γ RECEPTORS

Signed and Sealed this

Fifteenth Day of May, 2001

Attest:

NICHOLAS P. GODICI

Attesting Officer     Acting Director of the United States Patent and Trademark Office